(12) United States Patent
Werner et al.

(10) Patent No.: US 9,643,050 B2
(45) Date of Patent: May 9, 2017

(54) FITNESS ACTIVITY MONITORING SYSTEMS AND METHODS

(75) Inventors: Jon Harald Werner, Austin, TX (US); Christian DiBenedetto, North Plains, OR (US); Stephen John Black, Portland, OR (US); Amy Jones Vaterlaus, Portland, OR (US)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 13/335,545

(22) Filed: Dec. 22, 2011

(65) Prior Publication Data

US 2013/0166048 A1   Jun. 27, 2013

(51) Int. Cl.
*A63B 71/00*   (2006.01)
*A63B 24/00*   (2006.01)
(Continued)

(52) U.S. Cl.
CPC ...... *A63B 24/0062* (2013.01); *A61B 5/02055* (2013.01); *A61B 5/4875* (2013.01); *G01S 19/19* (2013.01); *G06Q 10/10* (2013.01); *G06Q 30/0241* (2013.01); *G06Q 50/01* (2013.01); *H04L 67/12* (2013.01); *H04L 67/18* (2013.01); *A61B 5/02438* (2013.01); *A61B 5/0816* (2013.01); *A61B 5/112* (2013.01); *A61B 5/1112* (2013.01); *A61B 2562/0219* (2013.01);
(Continued)

(58) Field of Classification Search
USPC ............ 463/6; 700/91; 482/51, 57, 74, 900, 482/902; 340/573.1
See application file for complete search history.

(56) References Cited

U.S. PATENT DOCUMENTS 7,254,516 B2   8/2007   Case, Jr. et al.
7,292,867 B2   11/2007   Werner et al.
(Continued)

FOREIGN PATENT DOCUMENTS

CN   101689304 A   3/2010
CN   101713660 A   5/2010
(Continued)

OTHER PUBLICATIONS

U.S. Appl. No. 13/335,629, inventors Werner et al., filed Dec. 22, 2011.
(Continued)

*Primary Examiner* — Masud Ahmed
(74) *Attorney, Agent, or Firm* — Sterne, Kessler, Goldstein & Fox P.L.L.C.

(57) ABSTRACT

Apparatus, systems, and methods for tracking the location of an individual during a fitness activity are disclosed. A method of tracking a participant engaged in a fitness activity includes determining a location of the participant during the fitness activity based on data received at a portable fitness device used by the participant; determining a location of a spectator during the fitness activity based on data received at a mobile spectator device used by the spectator; from a server, sending an alert to a spectator at a spectator device during the fitness activity indicating that the participant is within a predetermined distance of the spectator; and sending an alert to the portable fitness device during the fitness activity indicating that the spectator is within a predetermined distance of the participant.

32 Claims, 7 Drawing Sheets

::::

(51) Int. Cl.
  *G01S 19/19* (2010.01)
  *H04L 29/08* (2006.01)
  *G06Q 10/10* (2012.01)
  *G06Q 30/02* (2012.01)
  *G06Q 50/00* (2012.01)
  *A61B 5/0205* (2006.01)
  *A61B 5/00* (2006.01)
  *G06Q 50/22* (2012.01)
  *A61B 5/024* (2006.01)
  *A61B 5/08* (2006.01)
  *A61B 5/11* (2006.01)

(52) U.S. Cl.
  CPC ... *A61B 2562/0223* (2013.01); *A63B 2220/12* (2013.01); *A63B 2220/17* (2013.01); *A63B 2220/40* (2013.01); *A63B 2230/06* (2013.01); *A63B 2230/42* (2013.01); *A63B 2230/50* (2013.01); *G06Q 50/22* (2013.01)

(56) References Cited

U.S. PATENT DOCUMENTS

| | | | |
|---|---|---|---|
| 7,480,512 B2 | 1/2009 | Graham et al. | |
| 7,579,946 B2 | 8/2009 | Case, Jr. | |
| 7,603,255 B2 | 10/2009 | Case, Jr. et al. | |
| 7,607,243 B2 | 10/2009 | Berner, Jr. et al. | |
| 7,706,815 B2 | 4/2010 | Graham et al. | |
| 7,805,149 B2 | 9/2010 | Werner et al. | |
| 7,805,150 B2 | 9/2010 | Graham et al. | |
| 7,941,160 B2 | 5/2011 | Werner et al. | |
| 7,953,549 B2 | 5/2011 | Graham et al. | |
| 7,957,752 B2 | 6/2011 | Werner et al. | |
| 7,969,314 B2 | 6/2011 | Boyd et al. | |
| 8,015,732 B2 | 9/2011 | Berner, Jr. et al. | |
| 8,028,443 B2 | 10/2011 | Case, Jr. | |
| 8,068,858 B2 | 11/2011 | Werner et al. | |
| 8,086,421 B2 | 12/2011 | Case, Jr. et al. | |
| 8,112,251 B2 | 2/2012 | Case, Jr. et al. | |
| 8,188,868 B2 | 5/2012 | Case, Jr. | |
| 8,224,429 B2 | 7/2012 | Prstojevich et al. | |
| 8,244,226 B2 | 8/2012 | Werner et al. | |
| 8,244,278 B2 | 8/2012 | Werner et al. | |
| 8,248,247 B2 | 8/2012 | Boyd et al. | |
| 8,258,941 B2 | 9/2012 | Case, Jr. | |
| 8,260,667 B2 | 9/2012 | Graham et al. | |
| 8,350,708 B2 | 1/2013 | Case, Jr. | |
| 2005/0227811 A1 | 10/2005 | Shum et al. | |
| 2007/0006489 A1 | 1/2007 | Case, Jr. et al. | |
| 2007/0159926 A1 | 7/2007 | Prstojevich et al. | |
| 2008/0082254 A1 | 4/2008 | Huhtala | |
| 2009/0009398 A1 | 1/2009 | Taylor | |
| 2009/0075677 A1 | 3/2009 | Seger et al. | |
| 2009/0228157 A1* | 9/2009 | Breed | 701/1 |
| 2010/0088023 A1* | 4/2010 | Werner | 701/206 |
| 2011/0029611 A1* | 2/2011 | Hutchison et al. | 709/204 |
| 2011/0196603 A1 | 8/2011 | Graham et al. | |
| 2011/0238755 A1* | 9/2011 | Khan et al. | 709/204 |
| 2011/0250937 A1* | 10/2011 | Hubbard et al. | 463/6 |
| 2011/0314700 A1 | 12/2011 | Case, Jr. | |
| 2011/0314702 A1 | 12/2011 | Berner, Jr. et al. | |
| 2012/0035487 A1 | 2/2012 | Werner et al. | |
| 2012/0041767 A1* | 2/2012 | Hoffman | A63B 24/0059 705/1.1 |
| 2012/0078396 A1 | 3/2012 | Case, Jr. et al. | |
| 2012/0136689 A1* | 5/2012 | Ickman et al. | 705/7.19 |
| 2012/0265326 A1 | 10/2012 | Prstojevich et al. | |
| 2012/0293326 A1 | 11/2012 | Case, Jr. | |
| 2012/0299725 A1 | 11/2012 | Boyd et al. | |
| 2012/0303753 A1* | 11/2012 | Hansen | 709/217 |

FOREIGN PATENT DOCUMENTS

| | | |
|---|---|---|
| CN | 101890215 A | 11/2010 |
| CN | 102037375 A | 4/2011 |
| CN | 201906448 U | 7/2011 |
| DE | 102007040602 | 3/2009 |
| EP | 2 172 249 A2 | 4/2010 |
| JP | 2006-271611 A | 10/2006 |

OTHER PUBLICATIONS

European Search Report for Application No. EP 12198417, dated May 29, 2013, 4 pages.

Japanese Office Action dated Jul. 26, 2016 for Japanese Patent Appln. No. 2012-279257 (7 pages), with English Translation (5 pages).

* cited by examiner

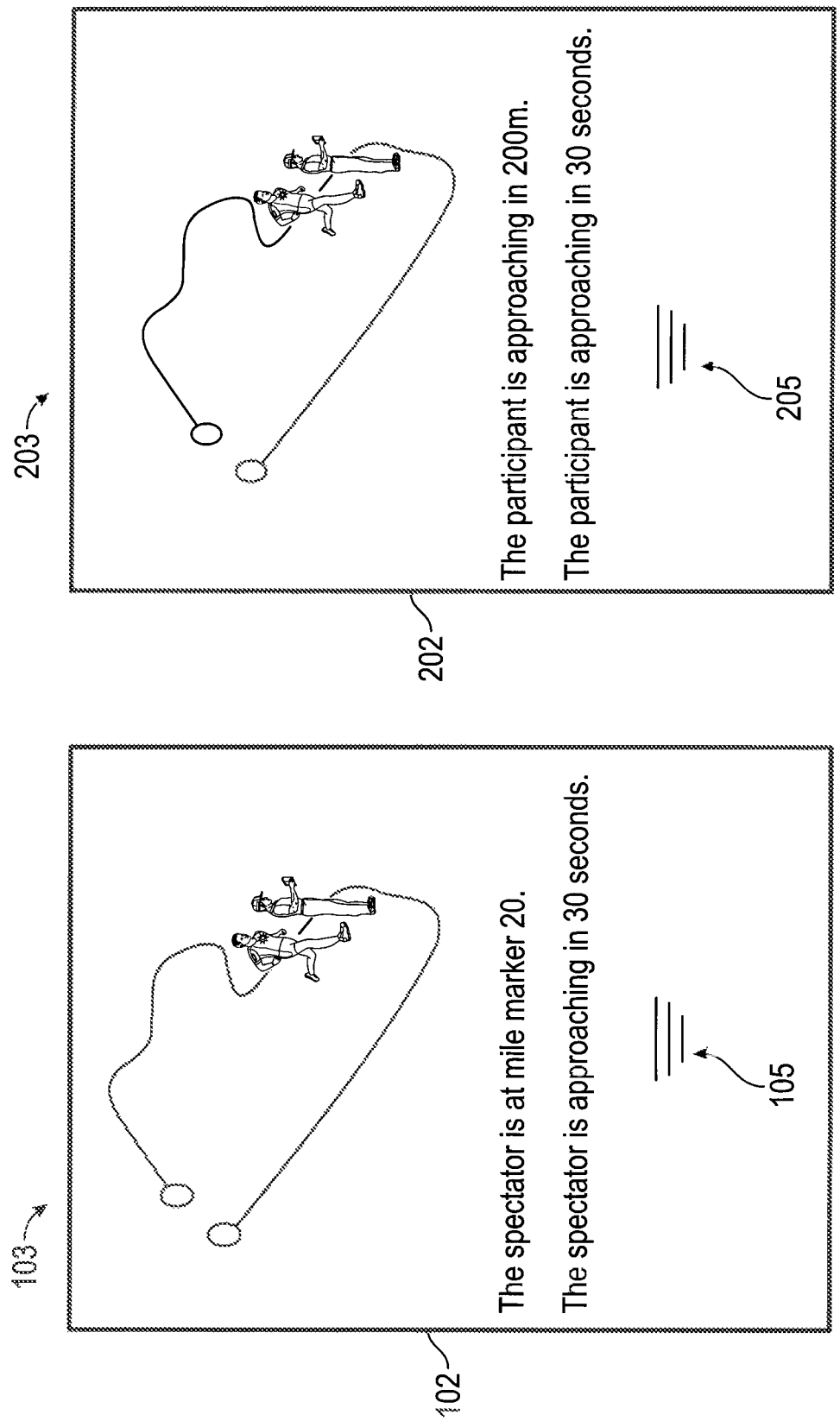

500 ─┐

┌─ 502
│ Determine a location of a fitness activity participant
│ during the fitness activity based on data received at
│ a portable fitness device used by the participant ┌─ 504
│ Send an alert to a spectator at a spectator device during
│ the fitness activity indicating that the participant is
│ within a predetermined distance or time of the spectator ┌─ 506
│ Send an alert to the portable fitness device during the
│ fitness activity indicating that the spectator is within
│ a predetermined distance or time of the participant

┌─ 602
│ Receive fitness activity registration information from a
│ spectator of a fitness activity, wherein the registration
│ information includes information about a participant in
│ the fitness activity ┌─ 604
│ Determine a location of the participant during the
│ fitness activity using a portable fitness device ┌─ 606
│ Send an alert to the portable fitness device during the
│ fitness activity indicating that a predetermined
│ spectator parameter threshold has been reached

FIG. 9

FITNESS ACTIVITY MONITORING SYSTEMS AND METHODS

BACKGROUND OF THE INVENTION

Field of the Invention

The present invention is directed to fitness activity monitoring. More particularly, embodiments of the present invention are directed to a system and method for monitoring the location of a fitness activity participant and/or a fitness activity spectator.

Background Art

Fitness activities can be rewarding to both participants and spectators. Participation in these activities can be important for maintaining a healthy lifestyle and individual well-being. Those that watch fitness activities may enjoy the excitement of the competition and may wish to show support or provide services for one or more participants. In this context, spectators may include, for example, coaches, trainers, supervisors, aid station attendants, or doctors. For example, improving the communication between participants and such spectators may be useful for supervising the physical condition of the participating athletes to achieve better performance or to provide medical services in order to prevent injuries or other health threats. Technology has resulted in the development of systems capable of monitoring the location and performance of individuals engaged in fitness activities. Fitness monitoring systems and methods are needed that provide real-time information to participants and spectators of these activities.

BRIEF SUMMARY OF THE INVENTION

Embodiments of the present invention relate to a method of tracking a participant engaged in a fitness activity. In an embodiment, the method includes: determining a location of the participant during the fitness activity based on data received at a portable fitness device used by the participant; determining a location of a spectator during the fitness activity based on data received at a mobile spectator device used by the spectator; from a server, sending an alert to a spectator at a spectator device during the fitness activity indicating that the participant is within a predetermined distance or time of the spectator or at a particular location or point of interest. The method may include sending an alert to the portable fitness device during the fitness activity indicating that the spectator is within a predetermined distance of the participant.

In another embodiment, a method of tracking an individual using a portable fitness device during a fitness activity, comprises: at a server, receiving fitness activity registration information from a spectator of a fitness activity, wherein the registration information includes information about a participant in the fitness activity; determining a location of the participant during the fitness activity using the portable fitness device; and sending an alert to the portable fitness device during the fitness activity that a predetermined spectator parameter threshold has been reached.

In another embodiment, a method of tracking a participant using a portable fitness device during a fitness activity, comprises: from a server, prior to the fitness activity sending an invitation to a spectator to participate in tracking the participant during the fitness activity, wherein the spectator is a member of a social network accessible by the spectator and the participant via the Internet; at a server, receiving an acceptance of the invitation from the spectator; determining a location of the participant during the fitness activity using the portable fitness device; and from a server, sending an alert to the portable fitness device during the fitness activity indicating that the spectator is within a predetermined distance of the participant. The method may include determining a location of the spectator during the fitness activity using a mobile spectator device. The method may include sending an alert to a spectator at a spectator device during the fitness activity indicating that the participant is within a predetermined distance of the spectator.

In another embodiment, a method of tracking a participant using a portable fitness device during a fitness activity, includes: from a server, prior to the fitness activity sending an invitation to a spectator to participate in tracking the participant during the fitness activity, wherein the spectator is a member of a social network accessible by the spectator and the participant via the Internet; at a server, receiving an acceptance of the invitation from the spectator; determining a location of the participant during the fitness activity using the portable fitness device; and from a server, sending an alert to a spectator at a spectator device during the fitness activity indicating that the participant is within a predetermined distance of the spectator.

In yet another embodiment, a method of tracking a participant engaged in a fitness activity, includes: determining a location of the participant during the fitness activity based on data received at a portable fitness device used by the participant; determining a location of a spectator during the fitness activity based on data received at a mobile spectator device used by the spectator; from a server, sending an alert to the portable fitness device during the fitness activity indicating that the spectator is within a predetermined distance of the participant.

In another embodiment, a computer program product comprising a non-transitory computer useable medium having computer program logic stored therein for causing one or more processors to track a participant engaged in a fitness activity includes: first computer readable program code for determining a location of the participant during the fitness activity based on data received at a portable fitness device used by the participant; second computer readable program code for determining a location of a spectator during the fitness activity based on data received at a mobile spectator device used by the spectator; and third computer readable program code for sending an alert to the portable fitness device during the fitness activity indicating that the spectator is within a predetermined distance of the participant. The methods described herein may be implemented in any combination of hardware and/or software, i.e., computer programs.

Embodiments of the present invention may include one or more features described in commonly owned U.S. Publication No. 2011/0082641, entitled "Methods and Computer Program Products for Providing Information About a User During a Physical Activity," U.S. patent application Ser. No. 12/836,421, filed Jul. 14, 2010 and entitled "Fitness Monitoring Methods, Systems and Program Products, and Applications Thereof," and U.S. patent application Ser. No. 12/836,416, filed Jul. 14, 2010 and entitled "Location-Aware Fitness Monitoring Methods, Systems, and Program Products, and Applications Thereof," the disclosures of which are hereby incorporated in their entirety by reference thereto.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

FIG. 3 is a schematic diagram of a fitness monitoring device display according to an embodiment of the present invention.

FIG. 4 is a schematic diagram of a spectator device display according to an embodiment of the present invention.

FIG. 8 is a flowchart depicting a method of tracking a fitness activity participant according to an embodiment of the present invention.

FIG. 9 is a flowchart depicting a method of tracking an individual according to an embodiment of the present invention.

DETAILED DESCRIPTION OF THE INVENTION

Figure 1:
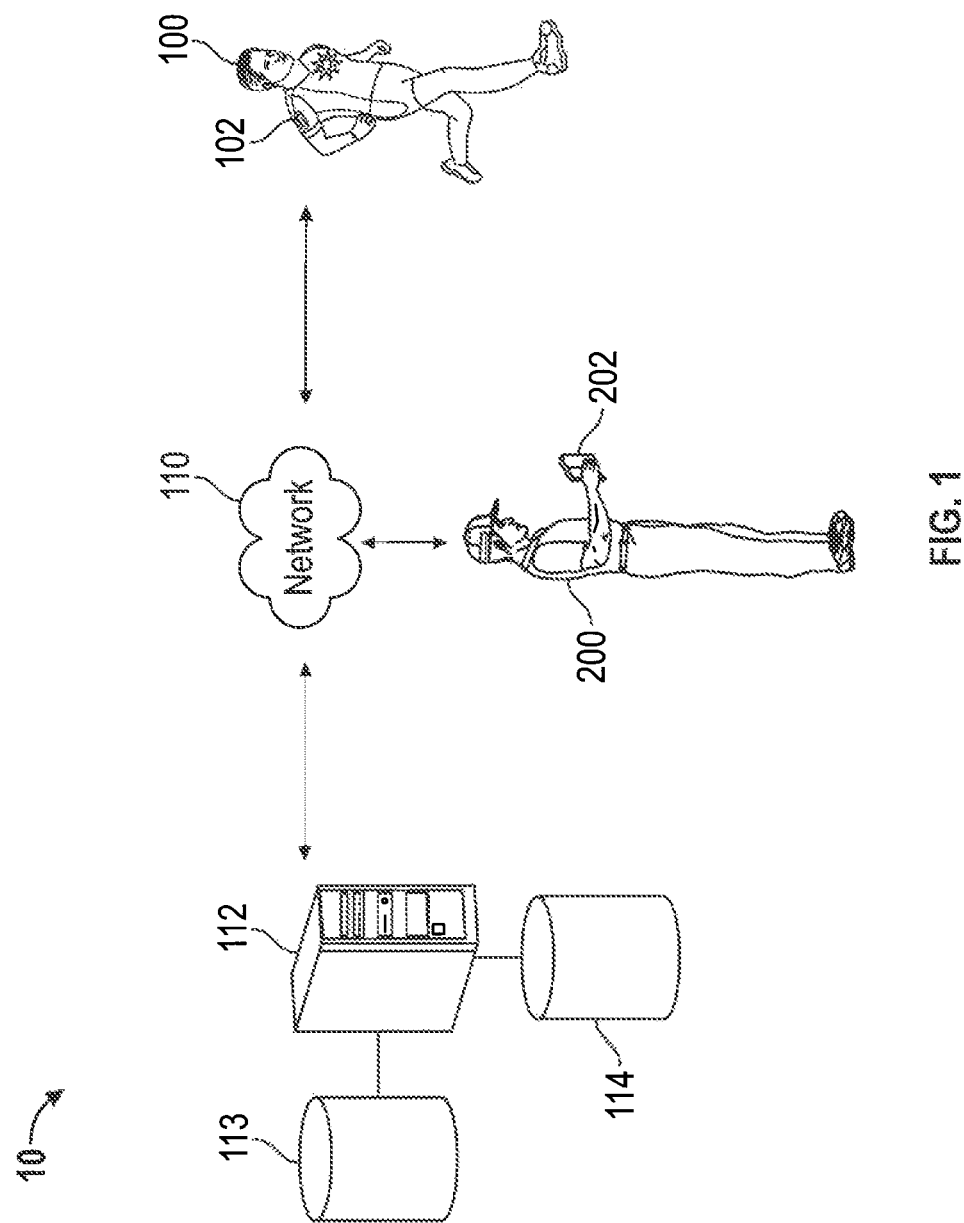
FIG. 1 is a schematic diagram of a fitness activity monitoring system according to an embodiment of the present invention.

The present invention will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present invention. Other suitable modifications and adaptations of the variety of conditions and parameters normally encountered in the field, and which would be apparent to those skilled in the art, are within the spirit and scope of the invention.

Embodiments of the present invention include a system 10 for monitoring the location of one or more individuals during a fitness activity. In various embodiments, the present invention includes a system 10 for monitoring the location of a participant (e.g., an athlete) 100 in a fitness activity and the location of a spectator 200 of a fitness activity. The spectator may include a coach, trainer, parent, supervisor, fan, aid station attendant, doctor, or other spectator of the fitness activity. In one embodiment, another participant may be a "spectator" as they may wish to track the performance of the participant 100. It will be understood that a spectator may not be physically viewing the participant or the race. During the fitness activity, the system 10 may send an alert to the spectator indicating that the participant is within a predetermined distance or time of reaching the spectator. During the fitness activity, the system may also send an alert to the participant 100 that the spectator 200 is within a predetermined distance or time of the participant. In this manner, embodiments of the present invention may provide real-time location awareness of the participant and/or spectator, and provide an enhanced participation or spectating experience of the fitness activity for individuals involved. For example, having been alerted that the participant they are tracking is approaching, an interested spectator may be informed to look for the participant and be ready to cheer on that individual or provide services (e.g., aid, water, equipment, etc.). Similarly, having been alerted that a spectator connected to the participant is approaching, a participant may be motivated or encouraged to perform during the fitness activity. Embodiments in which location alerts are provided to both the fitness activity participant 100 and the spectator 200 may increase the likelihood of the individuals being able to interact during the fitness activity.

With reference to FIG. 1, the system 10 includes a portable fitness monitoring device 102 used by a fitness activity participant 100 and adapted to determine and/or transmit the location of the participant during the fitness activity. The portable fitness monitoring device 102 is in communication with a fitness activity server 112 over a network 110 and may communicate the location of the participant 100 to the server 112. The system 10 further includes a spectator device 202 adapted to determine and/or transmit the location of the spectator 200 during the fitness activity. In one embodiment, the spectator device 202 is in communication with the fitness activity server 112 and/or the portable fitness monitoring device 102 over the network 110 and may communicate the location of the spectator 200 to the server 112 and/or the device 102.

In one embodiment, the portable fitness monitoring device 102 transmits an alert regarding the location of the participant 100 to the spectator device 202 directly, and the spectator device 202 transmits an alert regarding the location of the spectator 200 directly to the portable fitness monitoring device 102. In another embodiment, the server 112 transmits the alerts to the respective devices.

As will be appreciated by one of ordinary skill in the art, one or both of the portable fitness monitoring device 102 and the spectator device 202 include one or more processors adapted to implement application programs that provide the fitness monitoring methods described herein. In one embodiment, the fitness monitoring methods may be accessed and operated as a mobile application or "app" for a smartphone. For example, a fitness activity "Live Tracking" application may be downloaded to the portable fitness monitoring device 102 and the spectator device 202 from server 112 or a known smartphone application market. In some embodiments, a fitness activity "Live Tracking" application may be incorporated within another application, such as, for example, a fitness monitoring application.

As will be appreciated, a user may operate the "Live Tracking" application by selecting, for example, an icon on the portable fitness monitoring device 102 or the spectator device 202. For example, the user's touch or a touch gesture on the icon may initiate the application. The computer readable media for executing the application may be stored on the server 112 or in memory on the devices themselves, or combinations thereof. In other embodiments, the user may access a website provided by the server 112 to provide a portion or all of the fitness monitoring methods described herein. The version of the website accessible from the portable fitness monitoring device 102 and/or spectator device 202 may be simplified or otherwise modified to optimize it for display on a relatively small screen, such as, for example, the display of a smartphone or tablet computer.

The server 112 may be, for example, a telecommunication server, a web server, or other similar types of database servers. In an embodiment, server 112 may have multiple processors and multiple shared or separate memory components such as, for example, one or more computing devices incorporated in a clustered computing environment or server farm. The computing process performed by the clustered computing environment, or server farm, can be carried out across multiple processors located at the same or different locations. In an embodiment, server 112 can be implemented on a single computing device. In one embodiment, as shown in FIG. 1, the server 112 may include or be in communication with a fitness database 113 that may include an account of the participant 100 and/or spectator 200, a route database having stored route information, a training journal database having real-time or historical performance information regarding the workouts, performance and training of the participant 100, and/or a training plan database having a schedule of fitness activities scheduled for the participant 100 and/or spectator 200. For example, the fitness database 113 may include data storage according to embodiments described in U.S. Publication No. 2011/0082641, entitled "Methods and Computer Program Products for Providing Information About a User During a Physical Activity." The server 112 and/or fitness database 113 may include or provide access to a fitness website that provides access to an individual's account information and data. The website may provide an interface for performance data analysis and review, training scheduling, and other functionality regarding participant and/or spectator performance monitoring. Other individuals Who have access to or accounts with the fitness website may define an athlete community in which participants and spectators may interact. The server 112 may also include or be in communication with a social network database 114 related to the participant 100 and/or spectator 200, as discussed below.

The fitness activity may include any fitness activity engaged in by the participant 100 and viewed or attended by the spectator 200. In one embodiment, the fitness activity is a competitive fitness activity, including, but not limited to, a foot race, a bicycle race, a skiing or snowboarding race, or other fitness activity in which the physical location of the participant 100 changes as a function of time. For example, the fitness activity may comprise an organized competitive running race such as the New York City Marathon, the Army Ten Miler in Washington, D.C., or a high school cross-country race. In an embodiment, the fitness activity may be a self-organized activity. For example, a participant may organize a fitness activity to be engaged in with one or more individuals, such as family, friends, or members of a social network or fitness community.

In one embodiment, the fitness activity includes a predetermined route to be traversed by one or more participants. The predetermined route may be provided by a race organizer, for example, as would be the case for a competitive running race like the New York City Marathon. In some embodiments, the predetermined route may comprise a route created and scheduled by the participant. For example, the predetermined route may be created and scheduled according to embodiments described in U.S. Publication No. 2011/0082641, entitled "Methods and Computer Program Products for Providing Information About a User During a Physical Activity." In one embodiment, the predetermined route may be created and scheduled, for example, to be a 5K race that takes place every Wednesday at the same location and time, and may be saved in the user's account on server 112. The server 112 may store information related to the fitness activity, including the predetermined route of the fitness activity, which may be downloaded to the portable fitness monitoring device 102 and the spectator device 202. In some embodiments, predetermined route information may be sent from server 112 and received by portable fitness monitoring device 102 in real-time. In some embodiments, the fitness activity may comprise a vehicle race, such as, for example, a car or boat race.

In an embodiment, the network 110 may be the internet. The internet is a worldwide collection of servers, routers, switches and transmission lines that employ the Internet Protocol (TCP/IP) to communicate data. In an alternate embodiment, the network may be a private network or intranet, such as, for example, a network dedicated to a particular fitness activity (e.g., the New York City Marathon). Other suitable communication networks may be used.

As will be appreciated by one of ordinary skill in the art, one or both of the portable fitness monitoring device 102 and the spectator device 202 may be a device such as, for example, a mobile phone, a smartphone, a dedicated fitness monitoring device, a sports watch, a personal digital assistant, a music file player (e.g. and MP3 player), a tablet computer, a laptop computer, an intelligent article for wearing (e.g. a fitness monitoring garment, wrist band, or watch), a dongle (e.g. a small hardware device that is capable of physically coupling to a first electronic device and/or wirelessly coupling to additional electronic devices), or any other suitable device dedicated or non-dedicated to providing the monitoring methods described herein. In one embodiment, the devices may be mounted to the body of the participant 100 or spectator 200. For example, the devices may be arm-mounted, chest-mounted, leg-mounted, or foot-mounted. In one embodiment, portable fitness monitoring device 102 and/or the spectator device 202 may be hand held.

In one embodiment, one or both of the portable fitness monitoring device 102 and the spectator device 202 comprise a global positioning system (GPS) equipped device. As shown, for example, in FIG. 2, the system 10 may include GPS satellites 20 that continuously emit GPS signals 22 which may allow the portable fitness monitoring device 102 and/or the spectator device 202 to continuously determine its position, velocity, and bearing according to known techniques. As will be appreciated, the fitness monitoring device 102 and the spectator device 202 may include the necessary UPS receiver/transmitter to receive and transmit location information. The portable fitness monitoring device 102 and the spectator device 202 may continuously transmit their location to the server 112 or the other respective device, or may transmit at a predetermined interval for power saving purposes. In one embodiment, the portable fitness monitoring device 102 and the spectator device 202 may only transmit location information after predetermined criteria have been met. For example, the location transmission may be based on one or more alert parameter, as described below.

Figure 2:
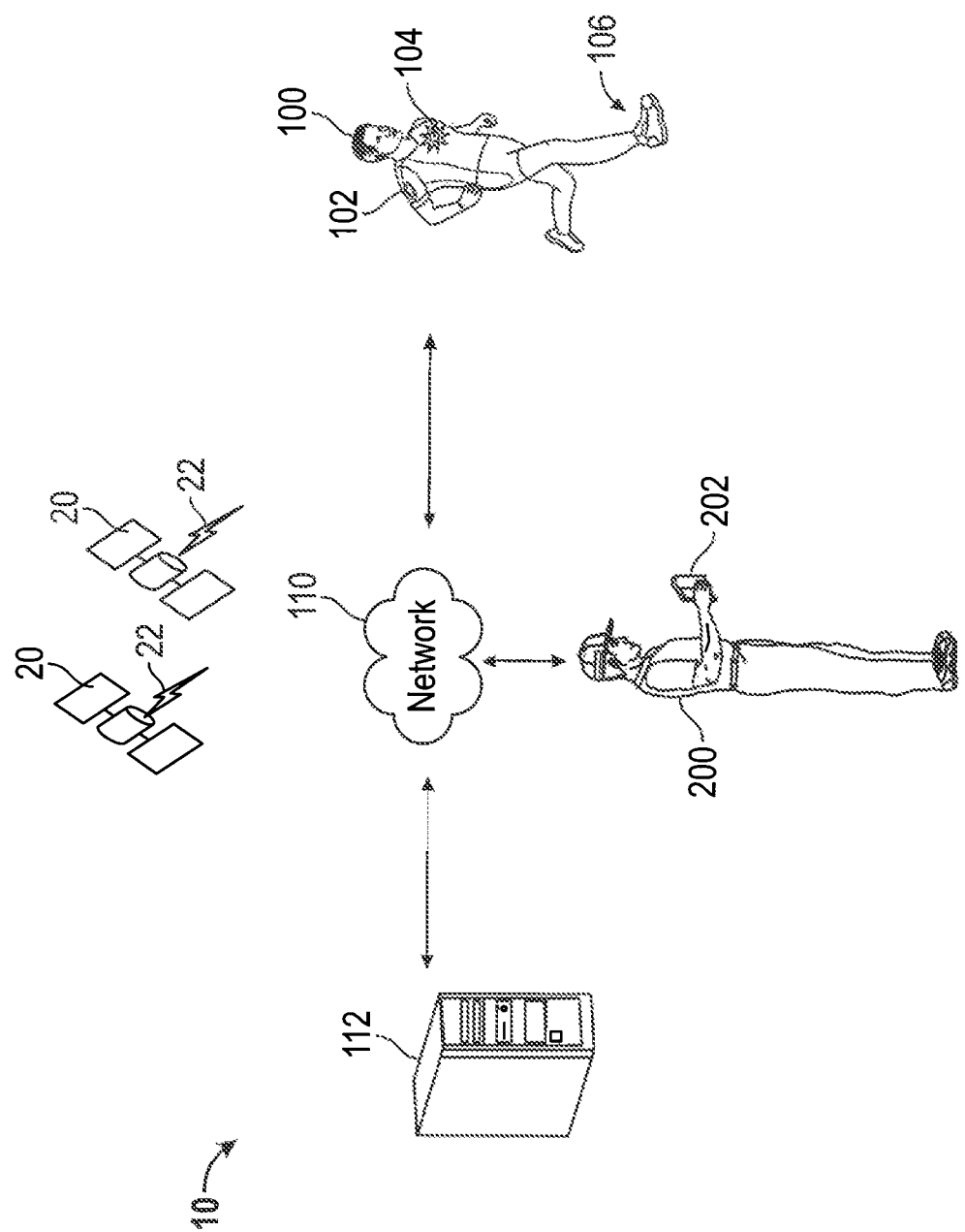
FIG. 2 is a schematic diagram of a GPS-based fitness activity monitoring system according to an embodiment of the present invention.

The portable fitness device 102 may also be adapted to measure or receive data regarding various performance parameters associated with the participant's performance during the fitness activity. As shown in FIG. 2, in one embodiment the system 10 may include one or more additional sensors 104 and 106 for measuring performance parameters of the participant 100. For example, the system 10 may include a heart rate sensor 104 for determining heart rate information during the fitness activity, and an accelerometer 106. In one embodiment, the accelerometer 106 may be used in conjunction with a GPS-enabled portable fitness monitoring device 102 to determine the location of the participant 100 according to known techniques. For example, data provided by the accelerometer 106 may be used to provide a "dead reckoning" of the participant's location when the GPS signal is interrupted (e.g., due to the participant traversing the route under a bridge). The system 10 may include other sensors including, but not be limited to, a pedometer, pulsimeter, breath rate sensor, gyroscope, magnetometer, hydration sensor, thermometers, or other suitable sensors for detecting information that may be used to measure and/or calculate performance parameters. Each of the sensors of the system 10 may be in communication with the portable fitness monitoring device 102 and may provide performance data regarding the participant 100 during the fitness activity. The sensors may be in wired or wireless communication. In one embodiment, the performance data may be transmitted from the portable fitness monitoring device 102 to the server 112 and/or the spectator device 202 over the network 110. In some embodiments the performance data is stored on the portable fitness monitoring device 102.

In some embodiments, devices such as a race mat placed along a predetermined route of the fitness activity may be used in conjunction with a GPS-enabled portable fitness monitoring device 102 to determine the location of the participant 100. For example, many organized races (e.g., New York City marathon) have a plurality of race mats disposed at predetermined distances along the predetermined route of the race. The race mats may be adapted to transmit time-stamped location data that may be received by the portable fitness monitoring device 102, for example. This data may be used in conjunction with GPS data to determine the location of the participant 100.

Alerts regarding the location of the participant 100 and spectator 200 may be sent to the individuals based on one or more predetermined alert parameters. These parameters may be set by the participant 100 and/or the spectator 200 prior to or during the fitness activity. For example, in embodiments that include a "Live Tracking" application, the application may provide an interface for defining the alert parameters. The alert parameters may be stored on the server 112 and accessed by the portable fitness monitoring device 102 and/or spectator device 202 over the network 110 (e.g., when a monitoring application is initiated), or may be stored on the devices themselves.

In one embodiment, the alert parameter may be distance based. For example, the participant 100 and/or spectator 200 may be alerted when the other is within a predetermined distance of their present location (e.g., 200 m). In one embodiment, the parameter may be time based and the participant 100 and/or spectator 200 may be alerted when the other is within a predetermined time of their present location. In one embodiment, this determination (i.e., estimated time of arrival) may be made based on the current location of the participant 100 and performance data received by the portable fitness monitoring device 102 from one or more receivers or sensors. For example, the estimated time of arrival may be based on the current pace of the participant 100, as determined by the GPS functionality of the portable fitness monitoring device 102 and/or the accelerometer 106, for example. In other embodiments, the estimated time of arrival may be based on the current location of the participant, a predetermined speed, and/or a predetermined pace of the participant.

In one embodiment, the location alert parameter may be based on other participant performance data received by the portable fitness monitoring device 102 from one or more receivers or sensors. For example, the parameter may be based on the measured heart rate of the participant 100. When the heart rate of the participant exceeds a predetermined value, this may be indicative that the participant is undergoing a difficult portion along the route of the fitness activity, for example. At this point, an alert may be sent to the participant 100 that the spectator 200 is only 2 miles away, thereby encouraging the participant to endure this portion of the route. Alerts to the participant 100 and/or the spectator 200 may be based on other performance data in combination with, or, alternatively, not in combination with, the current location of the participant 100 and/or the spectator 200.

The alerts provided to the participant 100 and/or the spectator 202 may be visual, audible, tactile, or any combination thereof. To provide these alerts, the portable fitness monitoring device 102 and the spectator device 202 are adapted to convey information to the user in this manner. With reference to FIGS. 3 and 4, in one embodiment the portable fitness monitoring device 102 and the spectator device 202 include a display 103, 203 and a speaker 105, 205, respectively. To provide a tactile alert, the devices may include a vibrating element (not shown), for example, or other suitable tactile element.

Figure 5:
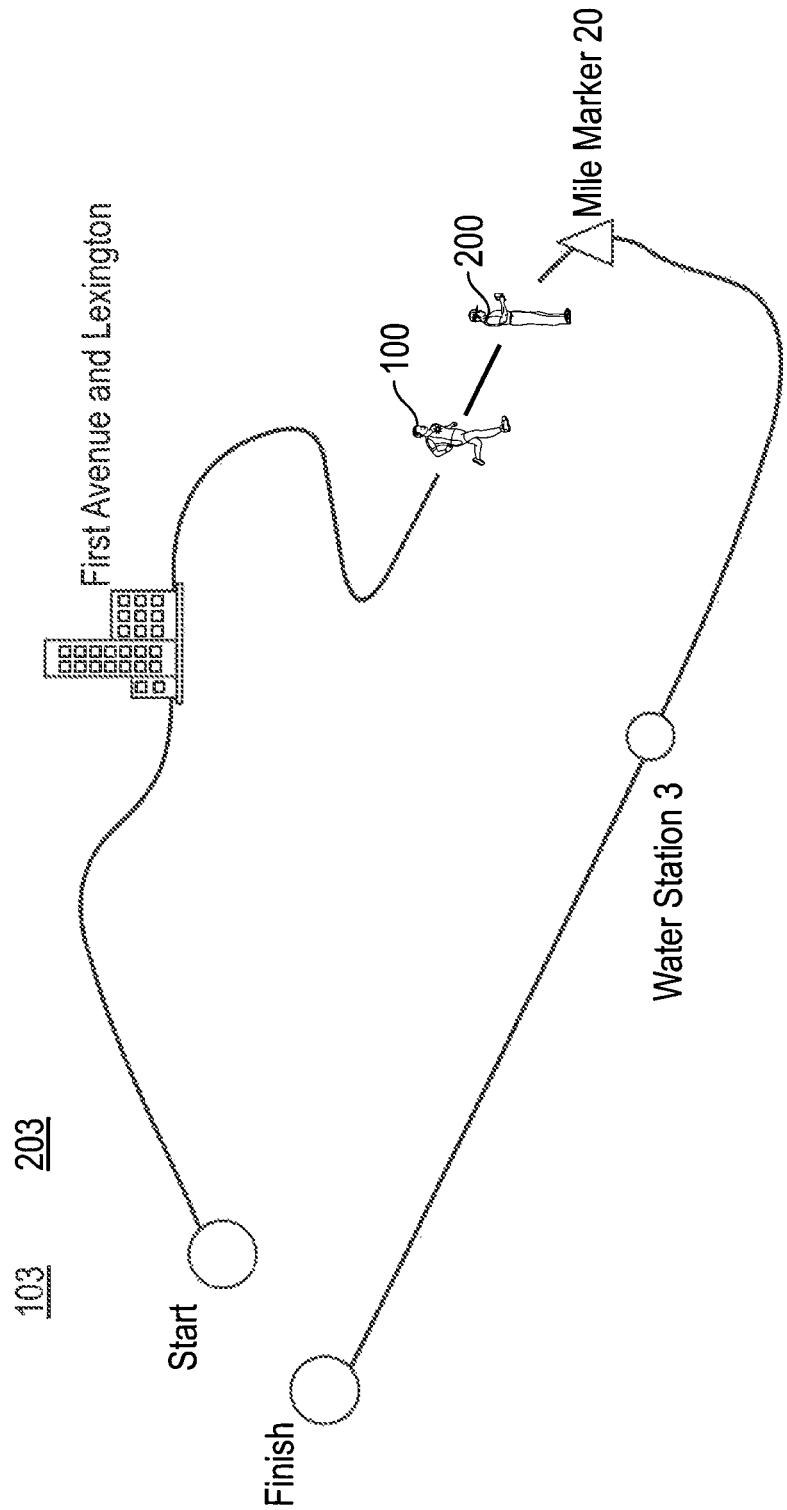
FIG. 5 is a schematic diagram of a fitness monitoring device display and/or a spectator device display according to an embodiment of the present invention.

A visual alert may visually indicate to the participant 100 and/or spectator 200 the other's location, as shown, for example, in FIGS. 3, 4, and 5. In one embodiment, the visual alert may include information about the fitness activity, such as, a map of the route of the fitness activity and may include one or more graphical symbols. The graphical symbols may provide specific location information and may provide an indication of the relative location between the participant and the spectator. In one embodiment, graphical symbols indicate the location of the participant 100 and the spectator 200 along the route. In one embodiment, for example, the visual alert may provide a precise location of where the spectator 200 is standing. In this manner, in some embodiments, the visual alert may include a detailed map (e.g., a Google satellite map) of the predetermined route of the fitness activity and the spectator's location superimposed on the map.

As the participant 100 continues to traverse the route, the graphical symbol may move accordingly in real-time on the display. In one embodiment, the depiction of the participant 100 and the spectator 200 may comprise a photo, avatar, or other symbol representative of the individual. The visual alert may include graphical symbols of landmarks along the course, such as, start line, finish line, mile markers, water stations, or streets and landmarks specific to a particular event (e.g., First Avenue and Lexington during the New York City Marathon). The graphical symbols, including photos and avatars, may be stored on server 112, fitness database 113, and/or social network database 114, for example. As shown in FIGS. 3 and 4, the visual alert may include text indicating that the participant 100 (or spectator 200) is approaching. For example, the text may indicate that "The spectator is approaching in 30 seconds," "The spectator is at mile marker 20," "The participant is approaching in 200 m," "The spectator is located on the east side of the race course at First Avenue and Lexington," or "The participant just crossed the finish line." In one embodiment, the visual alert may include one or more advertisements related to the fitness activity or the location of the participant 100 or spectator 200, for example.

An audible alert may audibly indicate to the participant 100 and/or spectator 200 that the other is approaching through device speaker 105, 205 or headphones (not shown), for example. In one embodiment, the audible alert may include a standard message that "The spectator is at mile marker 20" or "The participant is approaching in 30 seconds." In one embodiment, the audible alert may be a customized, pre-recorded message. For example, spectator 200 may pre-record a message such as "Keep it up John! I'll see you in one mile!" which may provide additional motivation and encouragement to the participant. Alerts may be stored on the respective devices 102, 202 or on server 112.

A tactile alert may also indicate to the participant 100 and/or spectator 200 that the other is approaching. For example, a vibrating element of the spectator device 202 may vibrate when the participant 100 is within 200 m or within a specific time, e.g., 20 seconds.

In one embodiment, visual, audible, and/or tactile alerts may be sent to the participant 100 and/or spectator 200 at predetermined intervals, locations, distances, or times that are unrelated to the location of the other. For example, an audible message may be sent to the participant 100 every 5 miles or 30 minutes of a race or when the participant or spectator arrives at a particular mile marker or landmark, for example.

In one embodiment, a participant 100 may receive alerts regarding other participants in the fitness activity. For example, the participant 100 may receive an alert that "You are one mile ahead of John," or "John just finished the race." In one embodiment, a spectator 200 may receive alerts regarding multiple participants 100, and the locations of multiple participants 100 may appear on a map at the spectator device 202.

Figure 6:
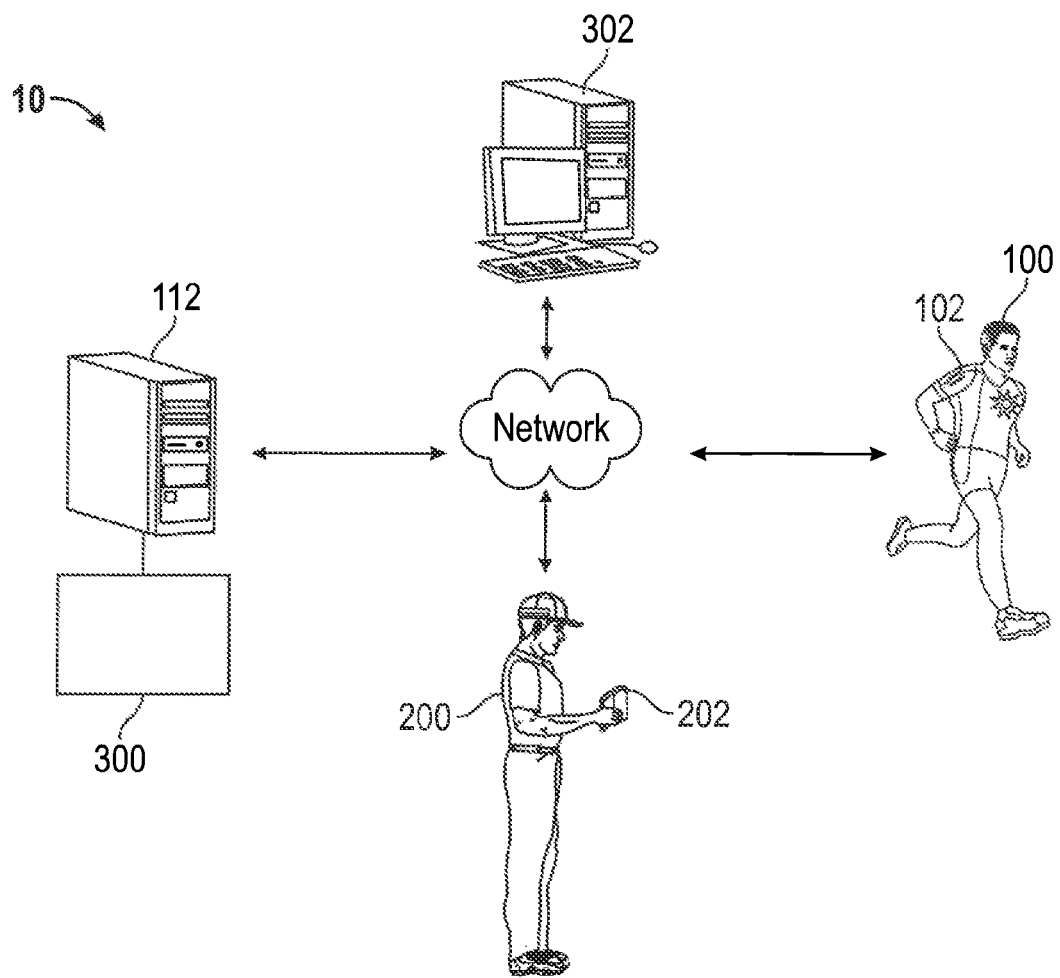
FIG. 6 is a schematic diagram of a fitness monitoring system including a registration interface according to an embodiment of the present invention.

In one embodiment, one or both of the participant 100 and spectator 200 may be registered to utilize the location and fitness monitoring methods described herein. In one embodiment, as shown in FIG. 6, for example, the participant 100 and/or spectator 200 may access a registration interface 300 (e.g., a website) on server 112 and provide registration information to server 112 from portable fitness monitoring device 102 and spectator device 202, respectively, or from another remote computing device 302. In embodiments that include a "Live Tracking" mobile application, the registration interface 300 may be provided as part of a smartphone application stored on the portable fitness monitoring device 102 or spectator device 202.

For example, a spectator 200 may be interested in tracking a participant 100 in real time during an upcoming fitness activity. In one embodiment, a spectator 200 may not be able to track the participant (e.g., receive location alerts during the fitness activity) without registering prior to the fitness activity. In one embodiment, the spectator 200 may access the registration interface 300 via the "Live Tracking" mobile application or website and provide registration information. The registration information may include information about the participant 100 that the spectator 200 wishes to track during the fitness activity. The participant information may include the participant's name, bib number, or other identifying information, for example. In one embodiment, the registration information may also include information about the spectator 200 that will allow the system 10 to communicate with the spectator during the fitness activity. The spectator information may include name, account information, email address, phone number, IP address, or other identification information. Other registration information, including, but not limited to, fitness activity information and payment information may be provided. In one embodiment, the registration interface 300 may be affiliated with the fitness activity. For example, the registration interface 300 may comprise the New York City Marathon website.

In one embodiment, participant 100 may invite one or more spectators 200 to track him or her during a fitness activity. In one embodiment, participant 100 may invite all or some members of a social network (e.g., Facebook®, LinkedIn®, Twitter®, etc.) to which participant may belong. For example, the participant 100 may send an invitation to his Facebook® friends, LinkedIn® contacts, or Twitter® followers to track him during an upcoming race. In one embodiment, the social network may comprise an athlete community associated with the participant's account on fitness database 113. In one embodiment, the spectators 200 may receive the invitation via their social network account on social network database 114. In embodiments that include a "Live Tracking" mobile application, an invitation indicator may be provided on the icon of the application, for example, indicating that the individual has an invitation to track a participant during a fitness activity. In other embodiments, spectators 200 may receive the invitation via email, text message, instant message, telephone call, or other suitable communication means. The spectator 200 may then accept the invitation. In some embodiments, the spectator 200 may track the participant 100 only after accepting the invitation. The acceptance may include spectator identification information that will allow the system 10 to communicate with the spectator during the fitness activity. In some embodiments, after accepting an invitation, the spectator may be required to register for tracking the participant during the fitness activity. In some embodiments, after registering or accepting an invitation, a participant or spectator may be required to download the mobile application from the server 112.

After the participant and/or spectator has registered and/or accepted an invitation, the system 10 may provide reminders to the user of the upcoming fitness activity. The reminder may be an indicator provided via the "Live Tracking" mobile application, or may be a message sent via other means, such as, for example, email, phone call, text message, instant messaging, and the like. The reminders may be provided at predetermined intervals such that the user may have a "countdown" to the upcoming fitness activity.

In one embodiment, the number of spectators 200 tracking the participant 100 during the fitness activity may be communicated to the participant. This spectator information may be based on the number of individuals who registered for tracking or accepted participant invitations, for example. The spectator information may be provided to the portable fitness monitoring device 102 audibly or visually before, during, or after the fitness activity. For example, before the fitness activity, participant 100 may receive a message at the portable fitness monitoring device 102 that "There are ten spectators registered to track you during the Race." During the fitness activity, participant 100 may receive an alert at the portable fitness monitoring device 102 that "There are twelve spectators watching you." along with a visual display of the location of each of the spectators. After the fitness activity, participant 100 may receive an alert that "Twenty spectators followed you during the Race." Spectator information for each participant 100 may be stored in the individual's account on the fitness database 113 for review and comparison. For example, members of an athlete community associated with fitness database 113 may compete to be the individual with the most fitness activity spectators or "followers."

In one embodiment, participant 100 may activate the live tracking feature to allow location information related to the participant 100 to be accessed by spectator 200 during the fitness activity. In one embodiment, activation may be conducted manually. For example, in one embodiment, participant 100 activates the tracking feature via the "Live Tracking" mobile application stored on the portable fitness monitoring device 102. In another embodiment, participant 100 activates the tracking feature via a website. In another embodiment, activation may occur automatically. For example, the live tracking feature may be automatically activated when the participant 100 is within a predetermined distance from the starting line of the fitness activity or on the race course: In one embodiment, participant 100 may receive visual or audible feedback that the live tracking feature is activated. In some embodiments, spectator 200 may also be required to activate the live tracking feature to allow location information related to the spectator 200 to be accessed by the participant 100 during the fitness activity. Activation of the live tracking feature may address privacy concerns.

After the live tracking feature has been activated, the system 10 may begin to record performance data from one or more sensors and receivers and may transmit participant location information. In one embodiment, the system 10 may only record and/or transmit data during the fitness activity. For example, if a particular race occurs on June 7 at 10 AM, the system 10 will begin recording and/or transmitting data at this time. In one embodiment, the system 10 may continue recording and/or transmitting for a predetermined amount of time, for example, based on an estimated time of completion by participant 100 (e.g., between 10 AM and 12:15 PM). The estimated time of completion may be provided as input by the participant prior to the fitness activity or may be based on historical data related to the participant or the fitness activity. In another embodiment, the participant 100 may manually stop the recording and/or transmitting at the completion of the fitness activity. In one embodiment, the recording of data may be provided as described in U.S. Publication No. 2011/0082641, entitled "Methods and Computer Program Products for Providing Information About a User During a Physical Activity," the disclosure of which is incorporated in its entirety by reference thereto.

Figure 7:
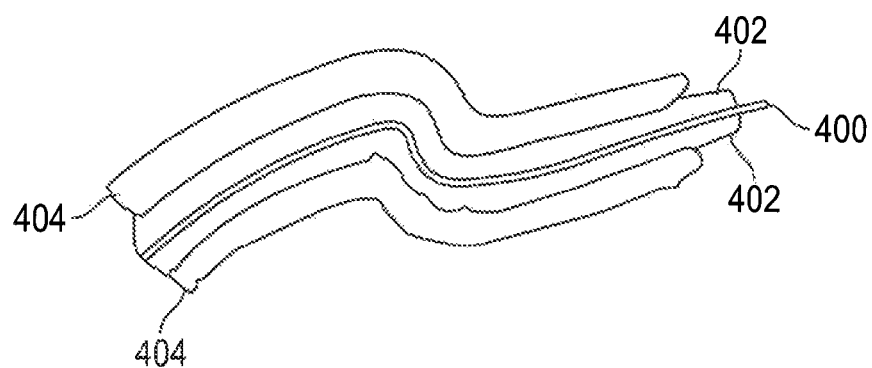
FIG. 7 is a schematic illustration of a fitness monitoring area according to an embodiment of the present invention.

In one embodiment, the system 10 may transmit the location of the participant 100 and/or record participant performance data based on predetermined parameters. For example, with reference to FIG. 7, the system 10 may only transmit the location of the participant when he is within a predetermined transmission/recording area 402 of the route 400 of the fitness activity. In one embodiment, the system 10 will not transmit participant location information in the area 404 outside of the transmission/recording area 402. The system may also not record participant performance data in the area 404. In this manner, participants may be prevented from cheating during the fitness activity by taking a shorter or less challenging route outside the predetermined route 400. In addition, the privacy of the participant may be maintained by restricting the transmission/recording area 402. Similar restricted transmission areas may be applied to the spectator device 202.

The portable fitness monitoring device 102, the spectator device 202, and the fitness activity server 112 are adapted to interact with one another to provide the fitness monitoring methods of the present invention. FIG. 8 is a process flowchart for a method 500 of tracking a participant engaged in a fitness activity according to an embodiment of the present invention. Method 500 may include at least steps 502, 504, and 506. Embodiments of system 10, as described herein will be used to describe method 500, but the method is not intended to be limited thereto. Step 502 includes determining a location of a fitness activity participant 100 during the fitness activity based on data received at a portable fitness monitoring device 102 used by the participant. During the fitness activity, in one embodiment the location of the participant 100 is continuously determined by the portable fitness monitoring device 102, and the location of the participant 100 is transmitted to the fitness activity server 112. In one embodiment, the location of the participant 100 is continuously transmitted to the server 112. In other embodiments, the participant's location may be transmitted at other predetermined intervals or based on predetermined criteria. In step 504, based on the location data received from the portable fitness monitoring device 102, the system 10 sends an alert to a spectator 200 at a spectator device 202 during the fitness activity indicating that the participant is within a predetermined distance or time of reaching the spectator or is at a particular location or point of interest along the route. The system 10 may also determine the location of the spectator during the fitness activity based on data received at a spectator device 202 used by the spectator. In step 506, based on the location data from the spectator device 202, the system 10 may also send an alert to the participant 100 at the portable fitness monitoring device 102 that the spectator 200 is within a predetermined distance or time of the participant 100 or at a particular location or point of interest along the route.

FIG. 9 is a process flowchart for a method 600 of tracking an individual using a portable fitness monitoring device 102 during a fitness activity according to an embodiment of the present invention. Method 600 may include at least steps 602, 604, and 606. Embodiments of system 10, as described herein will be used to describe method 600, but the method is not intended to be limited thereto. Step 602 includes receiving fitness activity registration information from a spectator 200 of a fitness activity. The registration information may include information about the participant 100 that the spectator 200 wishes to track during the fitness activity. In embodiments that include a "Live Tracking" mobile application, the registration information may be provided via a registration interface 300 that is provided by the application. Step 604 includes determining a location of the fitness activity participant 100 during the fitness activity based on data received at a portable fitness monitoring device 102 used by the participant. In step 606, the system sends an alert to the portable fitness monitoring device 102 during the fitness activity indicating that a predetermined spectator parameter threshold has been reached. For example, the participant 100 may be alerted that the spectator 200 is within a predetermined distance of their present location (e.g., 200 m) or within a predetermined time of their present location. The alert provided to the participant 100 may be visual, audible, tactile, or any combination thereof.

Figure 10:
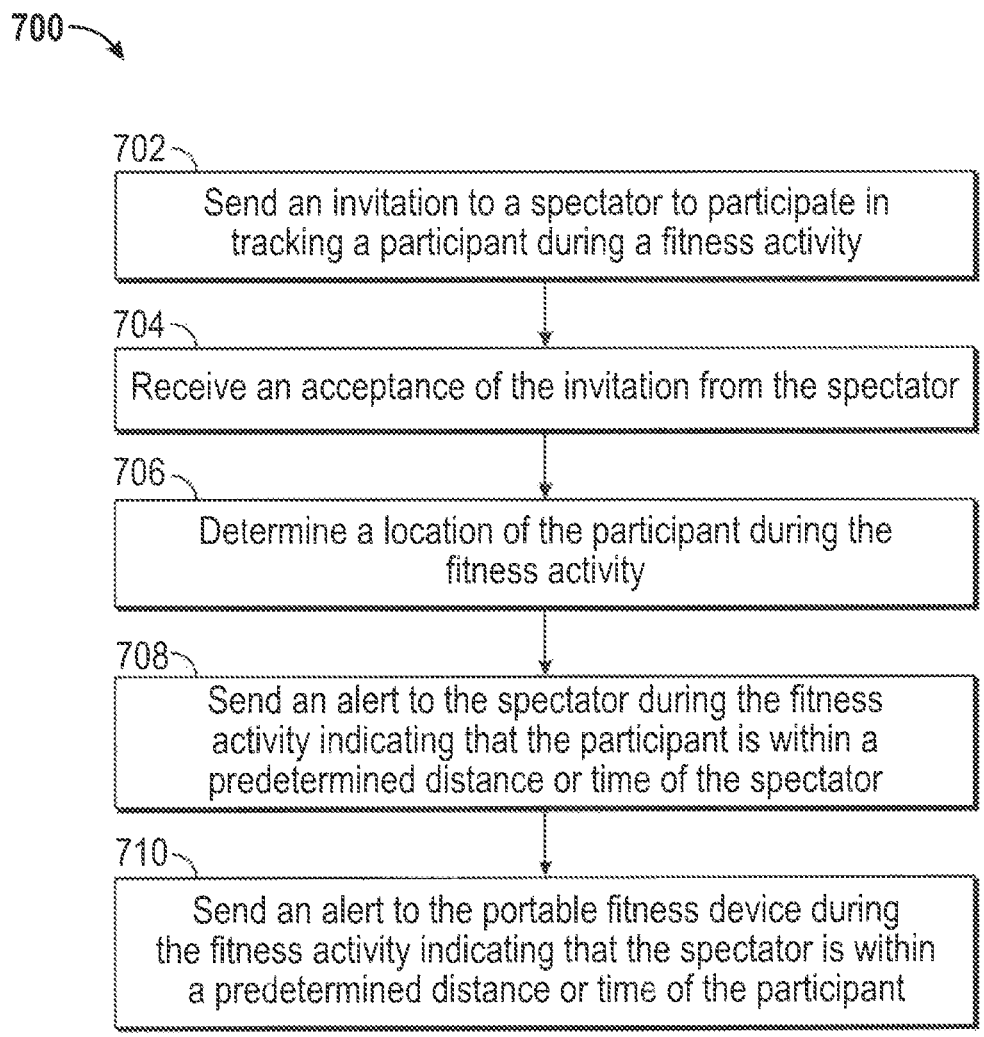
FIG. 10 is a flowchart depicting a method of tracking a fitness activity participant according to an embodiment of the present invention.

FIG. 10 is a process flowchart for a method 700 of tracking an individual using a portable fitness monitoring device 102 during a fitness activity according to an embodiment of the present invention. Method 700 may include at least steps 702, 704, 706, 708, and 710. Embodiments of system 10, as described herein will be used to describe method 700, but the method is not intended to be limited thereto. Step 702 includes sending an invitation to a spectator 200 to participate in tracking a participant 100 during a fitness activity. The invitation may be sent from the portable fitness monitoring device 102, for example. For example, the participant 100 may send an invitation to his Facebook® friends, LinkedIn® contacts, athlete community (e.g., on fitness database 113), or Twitter® followers to track him during an upcoming race. In step 704, an acceptance of the invitation is received from the spectator 200. The acceptance may be received at the server 112 or at the portable fitness monitoring device 102, for example. The acceptance may include spectator identification information that will allow the system 10 to communicate with the spectator during the fitness activity.

Step 706 includes determining a location of the participant 100 during the fitness activity. This determination may be based on data received at the portable fitness monitoring device 102 used by the participant. In step 708, based on the location data received at the portable fitness monitoring device 102, the system 10 sends an alert to the spectator 200 at a spectator device 202 during the fitness activity indicating that the participant is within a predetermined distance or time of reaching the spectator or is at a particular location or point of interest along the route. The system 10 may also determine the location of the spectator during the fitness activity based on data received at a spectator device 202 used by the spectator. In step 710, based on the location data received at the spectator device 202, the system 10 may also send an alert to the participant 100 at the portable fitness monitoring device 102 that the spectator 200 is within a predetermined distance or time of the participant or is at a particular location or point of interest along the route.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of tracking a pre-identified participant engaged in a fitness activity who is pre-identified by a spectator, comprising:
   determining a location of the pre-identified participant during the fitness activity based on data received at a portable fitness device used by the pre-identified participant;
   determining a location of the spectator during the fitness activity based on data received at a mobile spectator device used by the spectator;
   determining whether the spectator is registered to track the pre-identified participant; and
   if the spectator is registered to track the pre-identified participant, sending a first alert to the spectator at the spectator device during the fitness activity based on the spectator location and the pre-identified participant location, wherein the first alert indicates that the pre-identified participant is within a first predetermined distance of the spectator,
   wherein at least one of determining the location of the pre-identified participant, determining the location of the spectator, determining whether the spectator is registered to track the pre-identified participant, and sending the first alert is performed using at least one processor.

2. The method of claim 1, further comprising at a server, receiving pre-identified participant location information.

3. The method of claim 1, wherein the fitness activity includes a predetermined route.

4. The method of claim 1, wherein the fitness activity is a competitive event including a plurality of participants.

5. The method of claim 3, wherein the fitness activity is a marathon.

6. The method of claim 1, wherein the fitness activity is a fitness activity scheduled by the pre-identified participant.

7. The method of claim 1, wherein the fitness activity includes a route created by the pre-identified participant.

8. The method of claim 1, wherein the first alert is a visual alert.

9. The method of claim 1, wherein the first alert is an audible alert.

10. The method of claim 1, wherein the first alert is a tactile alert.

11. The method of claim 1, wherein the first alert indicates the distance from the spectator to the pre-identified participant.

12. The method of claim 1, wherein the first alert indicates an estimated time of arrival of the pre-identified participant at the spectator location.

13. The method of claim 1, wherein the data received at the portable fitness device and the data received at the mobile spectator device comprises at least one of global positioning system data and acceleration data.

14. The method of claim 1, comprising:
   receiving registration information from the spectator, wherein the registration information comprises spectator identification information,
   wherein determining that the spectator is registered to track the pre-identified participant comprises determining that the spectator is a member of the pre-identified participant's social network, the social network being accessible via the Internet.

15. The method of claim 1, wherein the pre-identified participant is a particular user identified prior to the fitness activity.

16. The method of claim 1, wherein the pre-identified participant is identified by name.

17. The method of claim 1, wherein the pre-identified participant is identified by bib number.

18. The method of claim 1, further comprising pre-identifying the participant based on identification by a first user of a particular second user to track, wherein the particular second user is the participant engaged in the fitness activity.

19. The method of claim 1, comprising:
   if the spectator is registered to track the pre-identified participant, sending a second alert to the portable fitness device during the fitness activity based on the spectator location and the pre-identified participant location, wherein the second alert indicates that the spectator is within a second predetermined distance of the pre-identified participant.

20. The method of claim 19, wherein the second alert indicates the spectator location.

21. A method of tracking a participant who is pre-identified by a spectator using a portable fitness device during a fitness activity, comprising:
prior to the fitness activity sending an invitation to the spectator to participate in electronically tracking the participant during the fitness activity
determining a location of the participant during the fitness activity using the portable fitness device;
determining a location of the spectator during the fitness activity using a mobile spectator device; and
sending a first alert to the spectator at the spectator device during the fitness activity based on the spectator location and the participant location, wherein the first alert indicates that the participant is within a first predetermined distance of the spectator, and wherein sending the first alert occurs after a determination that an acceptance of the invitation has been received,
wherein at least one of sending the invitation, determining the location of the participant, determining the location of the spectator, and sending the first alert is performed using at least one processor.

22. The method of claim 21, comprising:
sending a second alert to the portable fitness device during the fitness activity based on the spectator location and the participant location, wherein the second alert indicates that the spectator is within a second predetermined distance of the participant, and wherein sending the second alert only occurs in response to a determination that an acceptance of the invitation has been received.

23. The method of claim 21, wherein sending the first alert only occurs in response to a determination that an acceptance of the invitation has been received before a beginning of the fitness activity.

24. A computer program product comprising a non-transitory computer useable medium having computer program logic stored therein for causing one or more processors to track a pre-identified participant engaged in a fitness activity who is pre-identified by a spectator, the computer program logic comprising:
first computer readable program code for determining a location of the pre-identified participant during the fitness activity based on data received at a portable fitness device used by the pre-identified participant;
second computer readable program code for determining a location of the spectator during the fitness activity based on data received at a mobile spectator device used by the spectator;
third computer readable program code for determining whether the spectator is registered to track the pre-identified participant; and
fourth computer readable program code for sending a first alert to the spectator at the spectator device during the fitness activity if the spectator is registered to track the pre-identified participant, wherein the first alert is based on the spectator location and the pre-identified participant location, and wherein the first alert indicates that the pre-identified participant is within a first pre-determined distance of the spectator.

25. The computer program product of claim 24, comprising:
fifth computer readable program code for sending a second alert to the portable fitness device during the fitness activity if the spectator is registered to track the pre-identified participant, wherein the second alert is based on the location of the spectator and the location of the pre-identified participant, wherein the second alert indicates that the spectator is within a second predetermined distance of the pre-identified participant.

26. The method of claim 19, wherein the first predetermined distance is different from the second predetermined distance.

27. A method of tracking a participant engaged in a fitness activity who is pre-identified by a spectator, comprising:
determining a location of the participant during the fitness activity based on data received at a portable fitness device used by the participant;
determining a location of the spectator during the fitness activity based on data received at a mobile spectator device used by the spectator;
sending a first alert to the portable fitness device during the fitness activity based on the spectator location and the participant location, wherein the first alert indicates that the spectator is within a first predetermined distance of the participant; and
sending a second alert to the spectator at the spectator device during the fitness activity based on the spectator location and the participant location, wherein the second alert indicates that the participant is within a second predetermined distance of the spectator, wherein at least one of determining the location of the participant, determining the location of the spectator, sending the first alert, and sending the second alert is performed using at least one processor, and
wherein at least one of the first alert and the second alert is based on participant athletic performance data and provides a representation of the athletic performance data.

28. The method of claim 27, wherein the athletic performance data comprises heart rate data of the participant.

29. The method of claim 27, wherein the athletic performance data comprises acceleration data.

30. The method of claim 27, wherein the athletic performance data comprises at least one of pedometer data, pulsimeter data, breath rate data, gyroscope data, magnetometer data, hydration data, and thermometer data.

31. The method of claim 27, wherein the athletic performance data comprises heart rate data, and
wherein at least one of the first alert and the second alert is triggered by the heart rate data exceeding a heart rate threshold.

32. A method of tracking a participant engaged in a fitness activity who is pre-identified by a spectator, comprising:
determining a location of the participant during the fitness activity based on data received at a portable fitness device used by the participant, wherein the location of the participant is measured based on a position of the participant relative to a route;
determining a location of the spectator during the fitness activity based on data received at a mobile spectator device used by the spectator;
sending a first alert to the portable fitness device during the fitness activity based on the spectator location and the participant location, wherein the first alert indicates that the spectator is within a first predetermined distance of the participant; and
sending a second alert to the spectator at the spectator device during the fitness activity based on the spectator location and the participant location, wherein the second alert indicates that the participant is within a second predetermined distance of the spectator, wherein at least one of determining the location of the participant, determining the location of the spectator, sending the first alert, and sending the second alert is performed using at least one processor.

\* \* \* \* \*

UNITED STATES PATENT AND TRADEMARK OFFICE
CERTIFICATE OF CORRECTION

PATENT NO.          : 9,643,050 B2
APPLICATION NO.     : 13/335545
DATED               : May 9, 2017
INVENTOR(S)         : Werner et al.

Page 1 of 1

It is certified that error appears in the above-identified patent and that said Letters Patent is hereby corrected as shown below:

In the Claims

In Column 15, Line 8, Claim 21, delete "activity" and insert --activity;-- therefor.

Signed and Sealed this
Thirty-first Day of July, 2018

Andrei Iancu
*Director of the United States Patent and Trademark Office*